United States Patent
Fan et al.

(10) Patent No.: US 12,329,567 B2
(45) Date of Patent: Jun. 17, 2025

(54) CRANIAL ULTRASONIC STANDARD PLANE IMAGING AND AUTOMATIC DETECTION AND DISPLAY METHOD FOR ABNORMAL REGIONS

(71) Applicant: Shantou Institute of Ultrasonic Instruments Co., Ltd., Guangdong (CN)

(72) Inventors: Liexiang Fan, Guangdong (CN); Zehang Cai, Guangdong (CN); Bin Li, Guangdong (CN); Zhonghong Wu, Guangdong (CN); Yu Wang, Guangdong (CN); Jinhao Lin, Guangdong (CN); Xiaoming Zhou, Guangdong (CN); Shaohui Chen, Guangdong (CN); Weiwu Chen, Guangdong (CN); Jingfeng Guo, Guangdong (CN); Yijie Chen, Guangdong (CN); Zichun Chen, Guangdong (CN)

(73) Assignee: Shantou Institute of Ultrasonic Instruments Co., Ltd., Shantou (CN)

(*) Notice: Subject to any disclaimer, the term of this patent is extended or adjusted under 35 U.S.C. 154(b) by 489 days.

(21) Appl. No.: 17/964,776

(22) Filed: Oct. 12, 2022

(65) Prior Publication Data
US 2023/0225700 A1 Jul. 20, 2023

(30) Foreign Application Priority Data
Jan. 14, 2022 (CN) .......................... 2022100425985

(51) Int. Cl.
*A61B 8/08* (2006.01)
*A61B 8/00* (2006.01)
(Continued)

(52) U.S. Cl.
CPC ............ *A61B 8/0816* (2013.01); *A61B 8/145* (2013.01); *A61B 8/4477* (2013.01); *A61B 8/466* (2013.01);
(Continued)

(58) Field of Classification Search
CPC ..... A61B 8/0816; A61B 8/145; A61B 8/4477; A61B 8/466; A61B 8/0808; A61B 8/523;
(Continued)

(56) References Cited

PUBLICATIONS

Zhang, Lei "Automatic image quality assessment and measurement of fetal head in two dimensional ultrasound image" Journal of Medical Imaging. (Year: 2017).*

* cited by examiner

*Primary Examiner* — Molly Wilburn
(74) *Attorney, Agent, or Firm* — Calfee, Halter & Griswold LLP

(57) ABSTRACT

The present disclosure relates to the field of ultrasonic detection, in particular to a craniocerebral ultrasonic standard plane imaging and automatic detection and display method for abnormal regions. The following technical solution is adopted: contour detection is performed on the scanned ultrasound images the skull to construct a skull surface model, and the standard planes in ultrasound images are identified and extracted according to the skull surface model. The symmetry of the standard planes in ultrasound images is used to compare the similarity, so as to obtain the abnormal regions for segmentation and display. The advantages of the present disclosure are as follows: the skull surface model is constructed by detecting the cranial edge, and the coordinate system is established based on this model, thereby the standard planes in ultrasound images can be quickly identified from the scanned ultrasound images.

12 Claims, 9 Drawing Sheets

(51) Int. Cl.
*A61B 8/14* (2006.01)
*G06T 7/00* (2017.01)

(52) U.S. Cl.
CPC .. *G06T 7/0012* (2013.01); *G06T 2207/10136* (2013.01)

(58) Field of Classification Search
CPC ..... A61B 8/483; A61B 8/5223; A61B 8/5215; G06T 7/0012; G06T 2207/10136; G06T 2207/10132; G06T 2207/30016; G06T 7/11; G06T 7/13; G06T 11/00; G06T 17/30

See application file for complete search history.

CRANIAL ULTRASONIC STANDARD PLANE IMAGING AND AUTOMATIC DETECTION AND DISPLAY METHOD FOR ABNORMAL REGIONS

CROSS-REFERENCE TO RELATED APPLICATION

This application claims priority from the Chinese patent application 2022100425985 filed Jan. 14, 2022, the content of which are incorporated herein in the entirety by reference.

TECHNICAL FIELD

The present disclosure relates to the field of ultrasonic detection, in particular to a cranial ultrasound standard plane imaging and automatic detection and display method for abnormal regions.

BACKGROUND

Cranial ultrasound (or brain ultrasonography) is a routine clinical practice that is mainly used in the clinical monitoring of neonates. It is mainly used for intraventricular hemorrhage, peri-cerebral hemorrhage infarction, post-hemorrhagic ventricular dilatation, and post-hemorrhagic pericerebral leukomalacia/paralysis. In traditional techniques, sonographers rely on knowledge and experience to identify abnormalities in images. With the continuous development of computer technology, the use of computers to automatically analyze and diagnose images can reduce the burden and improve the efficiency of doctors' diagnosis. However, the traditional image processing technology and the current popular machine learning method are not ideal for analyzing and diagnosing cranial ultrasound images, and there are issues such as low recognition accuracy and error-prone.

SUMMARY

The purpose of the present disclosure is to provide a cranial ultrasound standard plane imaging and automatic detection and display method for abnormal regions, specifically to provide a method that can automatically identify and extract standard ultrasonic images by using cranial ultrasonic imaging, and utilize the symmetry of standard plane ultrasonic images to scan and segment abnormal regions for display.

In order to achieve the above-mentioned purpose, the present disclosure adopts the following technical solution: a cranial ultrasound standard plane imaging and automatic detection and display method for abnormal regions, comprising the following steps:

S01 using the ultrasound probe of the ultrasound imaging system to perform an ultrasound scan on the skull, constructing a skull surface model according to the ultrasound images obtained and displaying the model on the monitor of the ultrasound imaging system;

S02 on the ultrasound imaging system, identifying the mid-sagittal plane and the mid-coronal plane of the skull surface model according to the skull surface model constructed in step S01, marking the intersection of the mid-sagittal plane, the mid-coronal plane and the skull surface model as the coordinate origin, and establishing a coordinate system;

S03 on the ultrasound imaging system, marking the position of the set standard planes on the constructed skull surface model and the coordinate system, finding and extracting ultrasound images corresponding to multiple clinically defined standard plane positions from the scanned ultrasound images;

S04 using the image processing system of the ultrasound imaging system to perform calculation of the histogram or the grayscale co-occurrence matrix on the standard ultrasonic images extracted in step S03 and performing normalization to extract feature data;

S05 performing similarity comparison calculation between the extracted feature data and the reference feature data; and S06 extracting the grayscale value of the difference (if any) between the extracted feature data and the reference feature data, and using such value as a guide to segment and display the abnormal regions of the standard planes in ultrasound images, and display them on the monitor of the ultrasound imaging system.

Specifically, the reference feature data in step S05 is the feature data extracted according to step S04 from standard planes in ultrasound images without any anomalies as validated by clinical practice.

In another solution, when the standard plane ultrasound image extracted in step S03 is symmetrical with respect to the mid-sagittal or the mid-coronal plane, in step S04 the standard plane in ultrasound images is divided into two mutually symmetrical regions, then the histogram or the grayscale co-occurrence matrix is calculated respectively, and normalization is performed to extract the feature data; In step S05 the feature data extracted from the two mutually symmetrical regions of the standard planes in ultrasound images are used as reference feature data for similarity comparison calculation.

Specifically, in step S05 the feature data extracted from the two mutually symmetrical regions and the standard plane ultrasound images without any anomalies as validated by clinical practice are used for the calculation of similarity comparison according to the feature data extracted in step S04, and the abnormal region is segmented and displayed according to step S06 respectively.

Specifically, when constructing the skull surface model in step S01, the three dimensional (3D) ultrasound images of the skull are scanned, based on the acquired 3D ultrasound images, the skull surface model is scanned and constructed.

In another solution, when constructing the skull surface model in step S01, 2D ultrasound cranial images are scanned, by detecting the boundary between the skull and the internal cranial tissues with the grayscale or grayscale+ grayscale gradient values based on the acquired 2D ultrasound images, a complete skull surface model is constructed by filtering and fitting the boundary between the skull and the internal cranial tissues detected by multi-frame 2D ultrasound images.

The advantages of the present disclosure are as follows: the skull surface model is constructed by detecting the cranial edge, and the coordinate system is established based on this model, thereby the standard planes in ultrasound images can be quickly identified from the scanned ultrasound images; By using the symmetry of standard planes in ultrasound images to compare the similarity, the abnormal regions in the ultrasound images can be quickly and accurately identified, segmented and displayed, providing efficient and accurate image analysis for cranial ultrasound scanning.

DESCRIPTION OF THE EMBODIMENTS

Embodiment 1

An ultrasonic cranial standard plane imaging and an automatic detection and display method for abnormal regions is characterized by comprising the following steps:

S01 using the ultrasound probe of the ultrasound imaging system to perform an ultrasound scan on the skull, constructing a skull surface model according to the ultrasound images obtained and displaying the model on the monitor of the ultrasound imaging system;

S02 on the ultrasound imaging system, identifying the mid-sagittal plane and the mid-coronal plane of the skull surface model according to the skull surface model constructed in step S01, marking the intersection of the mid-sagittal plane, the mid-coronal plane and the skull surface model as the coordinate origin, and establishing a coordinate system;

S03 On the ultrasound imaging system, marking the position of the set standard planes on the constructed skull surface model and the coordinate system, finding and extracting ultrasound images corresponding to multiple clinically defined standard plane positions from the scanned ultrasound images;

S04 using the image processing system of the ultrasound imaging system to perform calculation of the histogram or the grayscale co-occurrence matrix on the standard ultrasonic images extracted in step S03 and performing normalization to extract feature data;

S05 performing similarity comparison calculation between the extracted feature data and the reference feature data; and S06 extracting the grayscale value of the difference (if any) between the extracted feature data and the reference feature data, and using such value as a guide to segment and display the abnormal regions of the standard planes in ultrasound images, and display them on the monitor of the ultrasound imaging system.

In this embodiment, the reference feature data in step S05 is the feature data extracted according to step S04 from standard planes in ultrasound images without any anomalies as validated by clinical practice.

Specifically, when constructing the skull surface model in step S01, the 3D ultrasound images of the skull can be scanned, based on the acquired 3D ultrasound images, the skull surface model is scanned and constructed; Or 2D ultrasound cranial images can be scanned, by detecting the boundary between the skull and the internal cranial tissues with the grayscale or grayscale+grayscale gradient values based on the acquired 2D ultrasound images, a complete skull surface model is constructed by filtering and fitting the boundary between the skull and the internal cranial tissues detected by multi-frame 2D ultrasound images.

Figure 1:
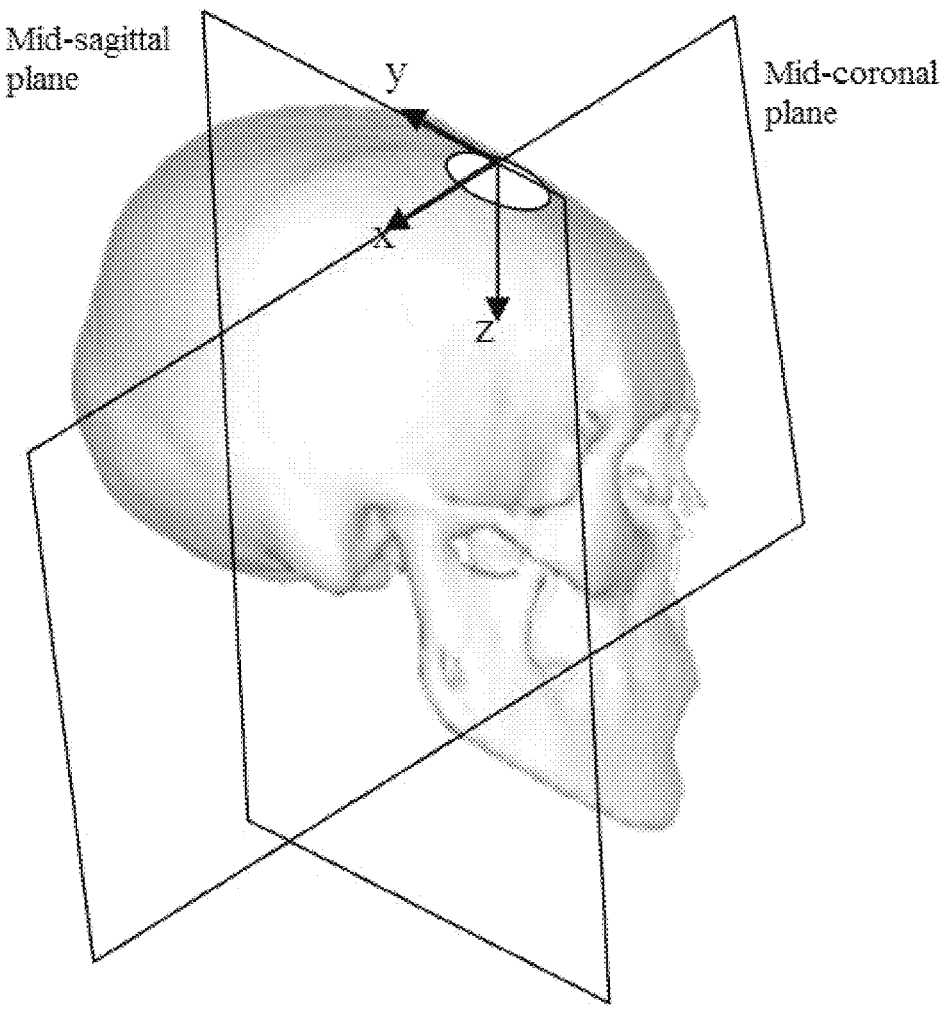
FIG. 1 illustrates a diagram showing the skull surface model in Embodiments 1 to 3, and the positional relation of the mid-sagittal plane, the mid-coronal plane and the coordinate system.
Figure 2:
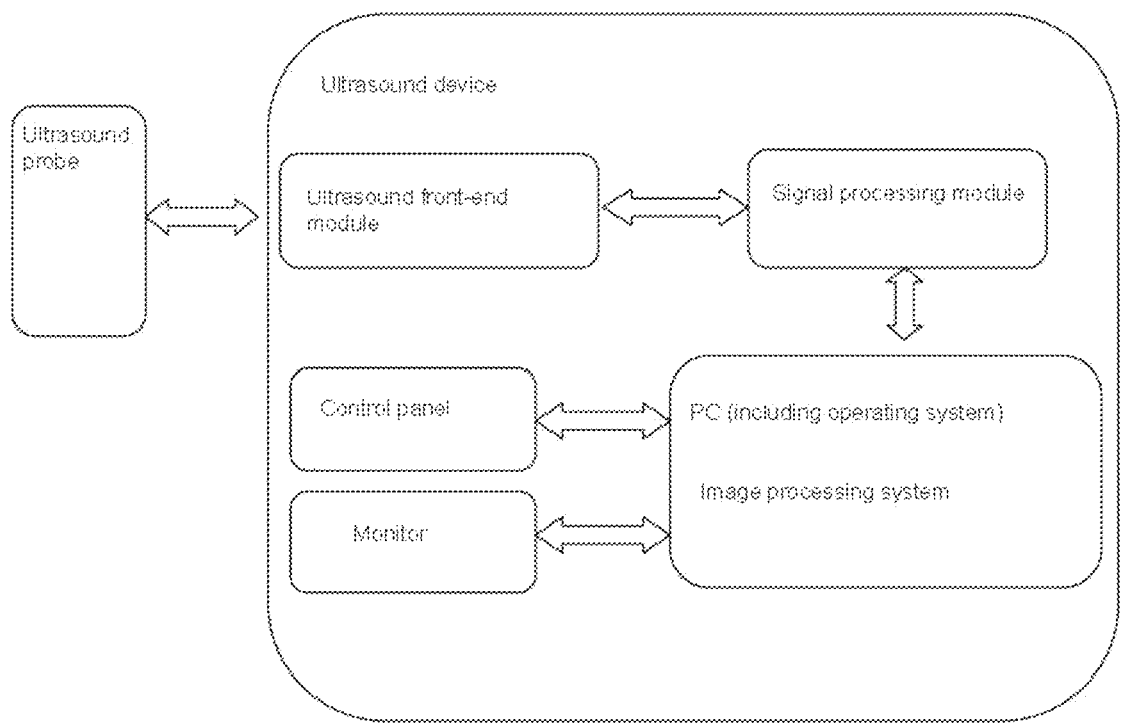
FIG. 2 illustrates the system connection schematic of the ultrasound imaging system used in Embodiments 1 to 3.
Figure 3:
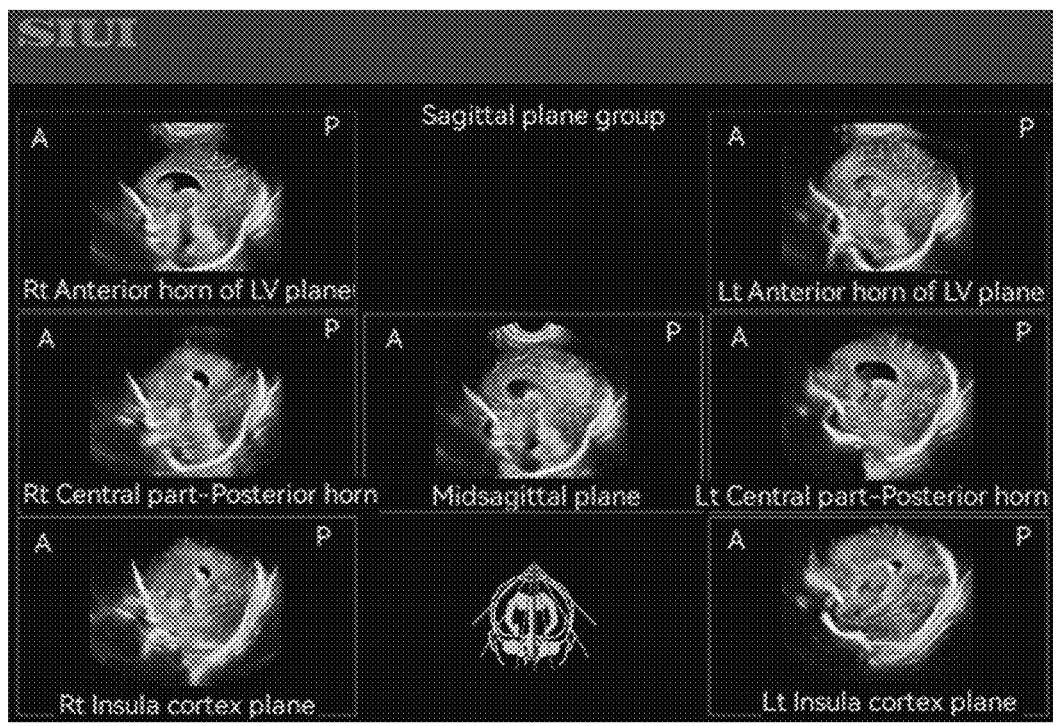
FIG. 3 illustrates a standard plane image of the cranial sagittal plane displayed on the ultrasound imaging system used in Embodiments 1 to 3.
Figure 4:
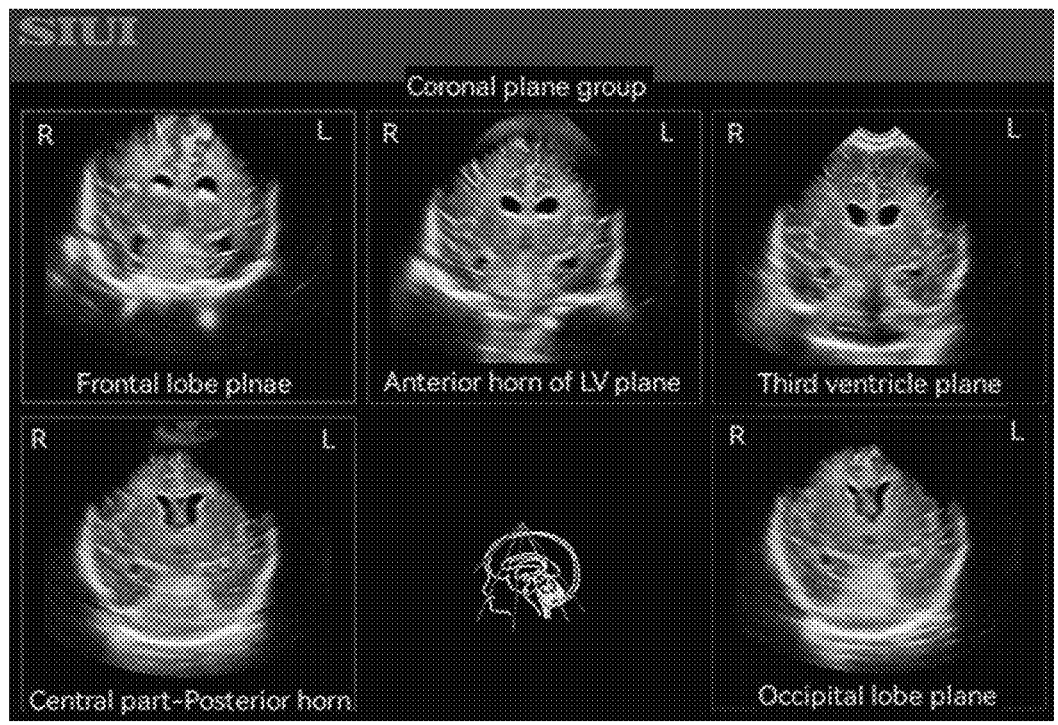
FIG. 4 illustrates a standard plane image of the cranial coronal plane displayed on the ultrasound imaging system used in Embodiments 1 to 3.

In the present embodiment, the system schematic diagram of the ultrasound imaging system in use is as shown in FIG. 2, which utilizes cranial ultrasound images collected by the ultrasound imaging system to construct a cranial curved surface model, and establishes coordinates on the cranial curved surface model. Therefore, ultrasound images for multiple clinically defined standard plane positions can be quickly found and extracted from the ultrasound images obtained by scanning, thereby improving the diagnostic efficiency. As shown in FIG. 3, it is the standard plane image of the cranial sagittal plane obtained by the method of this embodiment, and FIG. 4 is the standard plane image of the cranial coronal plane obtained by the method of this embodiment.

Embodiment 2

A cranial ultrasound standard plane imaging and automatic detection and display method for abnormal regions is characterized by comprising the following steps:

S01 using the ultrasound probe of the ultrasound imaging system to perform an ultrasound scan on the skull, constructing a skull surface model according to the ultrasound images obtained and displaying the model on the monitor of the ultrasound imaging system;

S02 on the ultrasound imaging system, identifying the mid-sagittal plane and the mid-coronal plane of the skull surface model according to the skull surface model constructed in step S01, marking the intersection of the mid-sagittal plane, the mid-coronal plane and the skull surface model as the coordinate origin, and establishing a coordinate system;

S03 on the ultrasound imaging system, marking the position of the set standard planes on the constructed skull surface model and the coordinate system, finding and extracting ultrasound images corresponding to multiple clinically defined standard plane positions from the scanned ultrasound images;

S04 using the image processing system of the ultrasound imaging system to perform performing calculation of the histogram or the grayscale co-occurrence matrix on the standard ultrasonic images extracted in step S03 and performing normalization to extract feature data;

S05 performing similarity comparison calculation between the extracted feature data and the reference feature data; and S06 extracting the grayscale value of the difference (if any) between the extracted feature data and the reference feature data, and using such value as a guide to segment and display the abnormal regions of the standard planes in ultrasound images, and display them on the monitor of the ultrasound imaging system.

Wherein, standard plane ultrasound images are generally symmetrical with respect to the mid-sagittal or mid-coronal plane, therefore when the standard plane ultrasound image extracted in step S03 is symmetrical with respect to the mid-sagittal or the mid-coronal plane, in step S04 the standard plane in ultrasound images is divided into two mutually symmetrical regions, then the histogram or the grayscale co-occurrence matrix is calculated respectively, and normalization is performed to extract the feature data; In step S05 the feature data extracted from the two mutually symmetrical regions of the standard planes in ultrasound images are used as reference feature data for similarity comparison calculation.

Specifically, when constructing the skull surface model in step S01, the 3D ultrasound images of the skull can be scanned, based on the acquired 3D ultrasound images, the skull surface model is scanned and constructed; Or 2D ultrasound cranial images can be scanned, by detecting the boundary between the skull and the internal cranial tissues with the grayscale or grayscale+grayscale gradient values based on the acquired 2D ultrasound images, a complete skull surface model is constructed by filtering and fitting the boundary between the skull and the internal cranial tissues detected by multi-frame 2D ultrasound images.

In the present embodiment, utilizing the symmetry of the standard plane image, the standard plane ultrasound image is divided into two mutually symmetric regions, respectively performing the calculation of the histogram or the gray scale co-occurrence matrix, and doing normalization processing to extract the feature data from the two mutually symmetrical regions of the standard plane ultrasonic image as reference feature data to perform similarity comparison calculation, so that the abnormal region can be quickly and accurately determined. In this embodiment, the standard images of the coronal plane that are symmetrical with respect to the mid-sagittal plane are selected for the test, and a total of 199 standard images of the coronal plane are selected, and the test of abnormal area detection is carried out according to the traditional method and the method adopted in this embodiment.

The result that traditional method detects is as follows:

| Coronal Standard Image | | A total of 199 cases 168 positive | 31 negative |
|---|---|---|---|
| Predictive value | Positive | 97 | 5 |
| | Negative | 71 | 26 |

The detection result of the method in this embodiment is as follows:

| Coronal Standard Image | | A total of 199 cases 168 positive | 31 negative |
|---|---|---|---|
| Predictive value | Positive | 151 | 4 |
| | Negative | 17 | 27 |

According to the results of the test above, the detection accuracy rate of positive image using the traditional method, namely sensitivity, is 57.7%, the detection accuracy rate of negative image, namely specificity is 83.9%, and the detection method of the present embodiment has a sensitivity of 89.9% and a specificity of 87.1%. For negative images, since there is no abnormal area, the specificity of the method in this embodiment is slightly higher than that of the traditional method, and the difference is not obvious. For positive images, the method in this embodiment has a higher accuracy in detecting abnormal areas than the traditional method. The former is significantly improved, with a sensitivity of 89.9% and a higher accuracy.

Figure 5A:
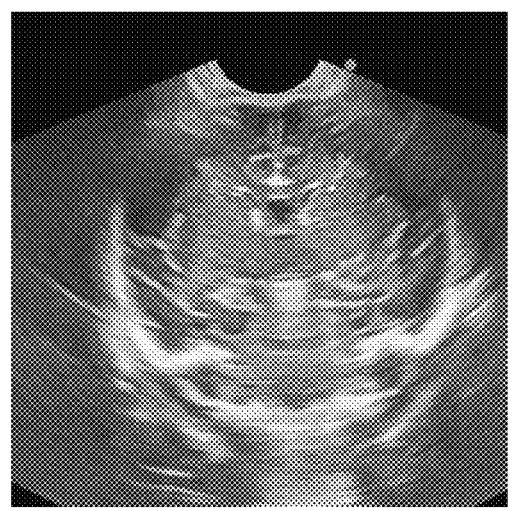
FIGS. 5-A, 5-B and 5-C illustrate the 1st group of original positive images, abnormal area detection result images, and abnormal area segmentation result images selected in Embodiment 2.
Figure 5B:
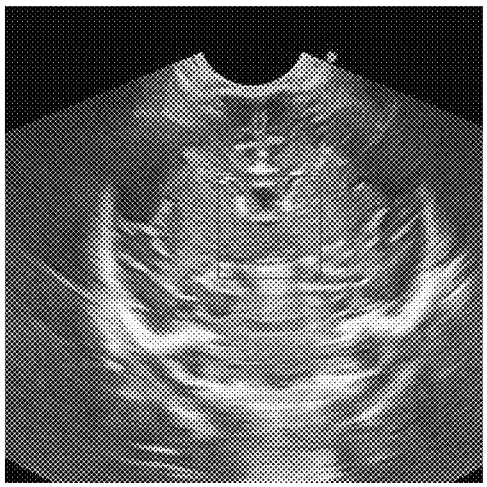
Figure 5C:
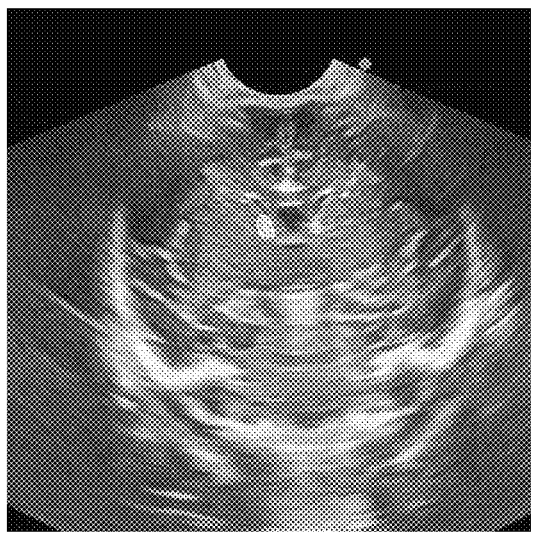
Figure 6A:
FIGS. 6-A, 6-B and 6-C illustrate the 2nd group of original positive images, abnormal area detection result images, and abnormal area segmentation result images selected in Embodiment 2.
Figure 6B:
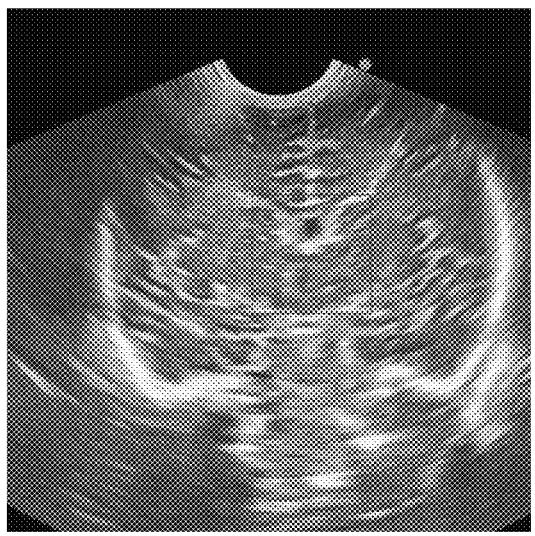
Figure 6C:
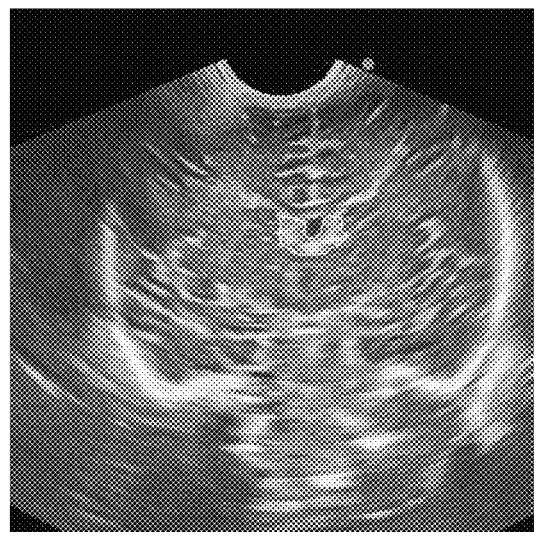
Figure 7A:
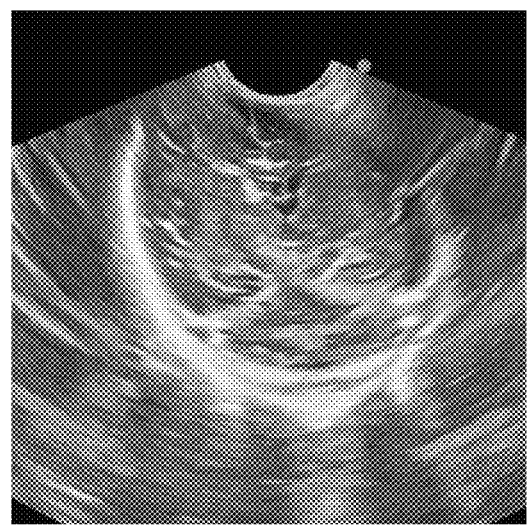
FIGS. 7-A, 7-B, and 7-C illustrate the 3rd group of original positive images, abnormal area detection result images, and abnormal area segmentation result images selected in Embodiment 2.
Figure 7B:
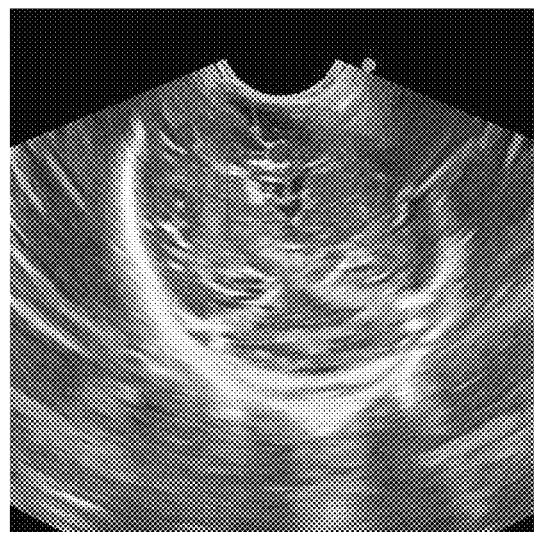
Figure 7C:
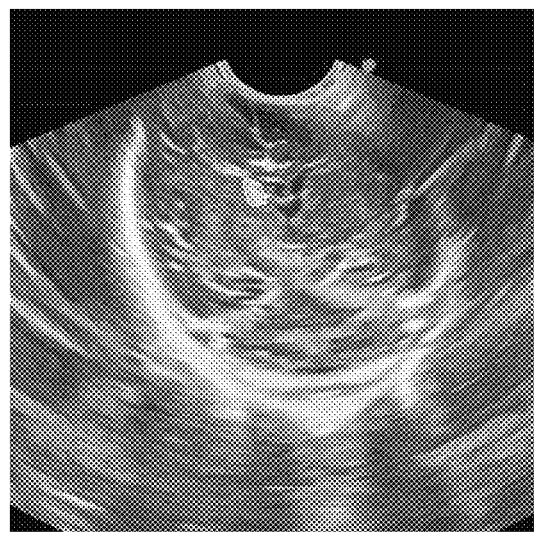
Figure 8A:
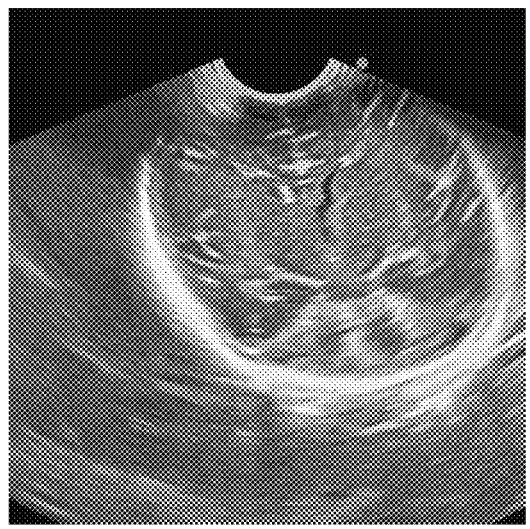
FIGS. 8-A, 8-B and 8-C illustrate the 4th group of original positive images, abnormal area detection result images, and abnormal area segmentation result images selected in Embodiment 2.
Figure 8B:
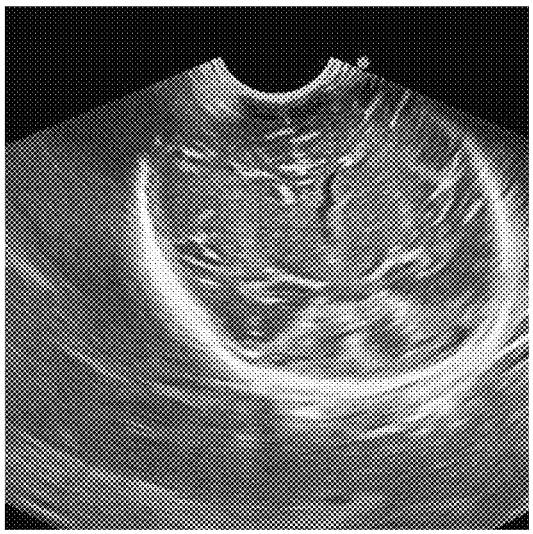
Figure 8C:
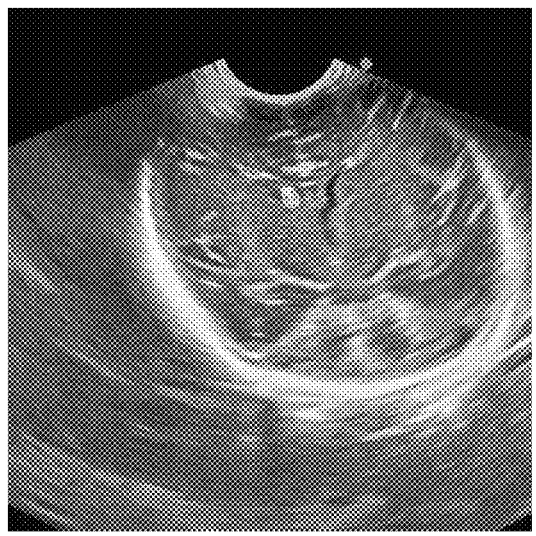

In addition, in the present embodiment, 4 groups of actual positive images are also extracted from the above experiments and is detected as negative in the traditional method; For the images detected as positive in the method of this embodiment, each group of images includes the original images, the abnormal area detection result output by the method of this embodiment, and the abnormal area segmentation result output by the method of this embodiment. See FIG. 5A, 5B, 5C; 6A, 6B, 6C; 7A, 7B, 7C; 8A, 8B and 8C.

Embodiment 3

A cranial ultrasound standard plane imaging and automatic detection and display method for abnormal regions, comprising the following steps:
S01 using the ultrasound probe of the ultrasound imaging system to perform an ultrasound scan on the skull, constructing a skull surface model according to the ultrasound images obtained and displaying the model on the monitor of the ultrasound imaging system;
S02 on the ultrasound imaging system, identifying the mid-sagittal plane and the mid-coronal plane of the skull surface model according to the skull surface model constructed in step S01, marking the intersection of the mid-sagittal plane, the mid-coronal plane and the skull surface model as the coordinate origin, and establishing a coordinate system;
S03 on the ultrasound imaging system, marking the position of the set standard planes on the constructed skull surface model and the coordinate system, finding and extracting the ultrasound images corresponding to multiple clinically defined standard plane positions from the scanned ultrasound images;
S04 using the image processing system of the ultrasound imaging system to perform calculation of the histogram or the gray scale co-occurrence matrix of the ultrasound image of the standard plane extracted in step S03 and performing normalization processing to extract feature data;
S05 performing similarity comparison calculation between the extracted feature data and the reference feature data; and
S06 extracting the grayscale value of the difference (if any) between the extracted feature data and the reference feature data, and using such value as a guide to segment and display the abnormal regions of the standard planes in ultrasound images, and display them on the monitor of the ultrasound imaging system.

Wherein, if the standard plane ultrasound image extracted in step S03 is symmetrical with respect to the mid-sagittal or the mid-coronal plane, in step S04 the standard plane in ultrasound images is divided into two mutually symmetrical regions, then the histogram or the grayscale co-occurrence matrix is calculated respectively, and normalization is performed to extract the feature data. In step S05 the feature data extracted from the two mutually symmetrical regions and the standard plane ultrasound images without any anomalies as validated by clinical practice are used for the calculation of similarity comparison according to the feature data extracted in step S04; Then, the feature data extracted from the two mutually symmetrical regions of the standard ultrasound image are used as mutual reference feature data for similarity comparison calculation; And then the two comparison methods are respectively used to segment and display the abnormal regions according to step S06, so as to obtain a more comprehensive and accurate abnormal region scanning result.

Specifically, when constructing the skull surface model in step S01, the 3D ultrasound images of the skull can be scanned, based on the acquired 3D ultrasound images, the skull surface model is scanned and constructed; Or 2D ultrasound cranial images can be scanned, by detecting the boundary between the skull and the internal cranial tissues with the grayscale or grayscale+grayscale gradient values based on the acquired 2D ultrasound images, a complete skull surface model is constructed by filtering and fitting the boundary between the skull and the internal cranial tissues detected by multi-frame 2D ultrasound images.

Certainly the embodiments above are preferred for the present disclosure only, but not intended to restrict the scope of use of the present disclosure. Therefore, any equivalent changes made on the principles of the present disclosure should be included in the protection scope of the present disclosure.

What is claimed is:

1. A cranial ultrasound standard plane imaging and automatic detection and display method for abnormal regions comprising the following steps:
    S01 Using the ultrasound robe of the ultrasound imaging system to perform an ultrasound scan on the skull, constructing a skull surface model according to the ultrasound images obtained and displaying the model on the monitor of the ultrasound imaging system;
    S02 on the ultrasound imaging system, identifying the mid-sagittal plane and the mid-coronal plane of the skull surface model according to the skull surface model constructed in step S01, marking the intersection of the mid-sagittal plane, the mid-coronal plane and the skull surface model as the coordinate origin, and establishing a coordinate system;
    S03 on the ultrasound imaging system, marking the position of the set standard planes on the constructed skull surface model and the coordinate system, identifying and extracting ultrasound images corresponding to multiple clinically defined standard plane positions from the scanned ultrasound images;
    S04 using the image processing system of the ultrasound imaging system to perform calculation of the histogram or the grayscale co-occurrence matrix on the standard ultrasonic images extracted in step S03 and performing normalization to extract feature data;
    S05 performing similarity comparison calculation between the extracted feature data and the reference feature data; and
    S06 extracting the grayscale value of the difference (if any) between the extracted feature data and the reference feature data, and using such value as a guide to segment the abnormal regions of the standard planes in ultrasound images, and display them on the monitor of the ultrasound imaging system.

2. The cranial ultrasound standard plane imaging and automatic detection and display method for abnormal regions according to claim 1, wherein reference feature data in step S05 is the feature data extracted according to step S04 from standard planes in ultrasound images without any anomalies as validated by clinical practice.

3. The cranial ultrasound standard plane imaging and automatic detection and display method for abnormal regions according to claim 1, wherein if the standard plane ultrasound image extracted in step S03 is symmetrical with respect to the mid-sagittal or the mid-coronal plane, in step S04 the standard plane in ultrasound images is divided into two mutually symmetrical regions, then the histogram or the grayscale co-occurrence matrix is calculated respectively, and normalization is performed to extract the feature data; In step S05 the feature data extracted from the two mutually symmetrical regions of the standard planes in ultrasound images are used as reference feature data for similarity comparison calculation.

4. The ultrasonic standard plane imaging and an automatic detection and display method for abnormal regions according to claim 3, wherein in step S05 the feature data extracted from the two mutually symmetrical regions and the standard plane ultrasound images without any anomalies as validated by clinical practice are used for the calculation of similarity comparison according to the feature data extracted in step S04, and the abnormal region is segmented and displayed according to step S06 respectively.

5. The ultrasonic standard plane imaging and automatic detection and display method for abnormal regions according to claim 1, wherein when constructing the skull surface model in step S01, the 3D ultrasound images of the skull are scanned, based on the acquired 3D ultrasound images, the skull surface model is scanned and constructed.

6. The ultrasonic standard plane imaging and an automatic detection and display method for abnormal regions according to claim 1, wherein when constructing the skull surface model in step S01, two dimensional (2D) ultrasound cranial images are scanned, by detecting the boundary between the skull and the internal cranial tissues with the grayscale or grayscale+grayscale gradient values based on the acquired 2D ultrasound images, a complete skull surface model is constructed by filtering and fitting the boundary between the skull and the internal cranial tissues detected by multi-frame 2D ultrasound images.

7. The ultrasonic standard plane imaging and automatic detection and display method for abnormal regions according to claim 2, wherein when constructing the skull surface model in step S01, the 3D ultrasound images of the skull are scanned, based on the acquired 3D ultrasound images, the skull surface model is scanned and constructed.

8. The ultrasonic standard plane imaging and automatic detection and display method for abnormal regions according to claim 3, wherein when constructing the skull surface model in step S01, the 3D ultrasound images of the skull are scanned, based on the acquired 3D ultrasound images, the skull surface model is scanned and constructed.

9. The ultrasonic standard plane imaging and automatic detection and display method for abnormal regions according to claim 4, wherein when constructing the skull surface model in step S01, the 3D ultrasound images of the skull are scanned, based on the acquired 3D ultrasound images, the skull surface model is scanned and constructed.

10. The ultrasonic standard plane imaging and an automatic detection and display method for abnormal regions according to claim 2, wherein when constructing the skull surface model in step S01, two dimensional (2D) ultrasound cranial images are scanned, by detecting the boundary between the skull and the internal cranial tissues with the grayscale or grayscale+grayscale gradient values based on the acquired 2D ultrasound images, a complete skull surface model is constructed by filtering and fitting the boundary between the skull and the internal cranial tissues detected by multi-frame 2D ultrasound images.

11. The ultrasonic standard plane imaging and an automatic detection and display method for abnormal regions according to claim 3, wherein when constructing the skull surface model in step S01, two dimensional (2D) ultrasound cranial images are scanned, by detecting the boundary between the skull and the internal cranial tissues with the grayscale or grayscale+grayscale gradient values based on the acquired 2D ultrasound images, a complete skull surface model is constructed by filtering and fitting the boundary between the skull and the internal cranial tissues detected by multi-frame 2D ultrasound images.

12. The ultrasonic standard plane imaging and an automatic detection and display method for abnormal regions according to claim 4, wherein when constructing the skull surface model in step S01, two dimensional (2D) ultrasound cranial images are scanned, by detecting the boundary between the skull and the internal cranial tissues with the grayscale or grayscale+grayscale gradient values based on the acquired 2D ultrasound images, a complete skull surface model is constructed by filtering and fitting the boundary between the skull and the internal cranial tissues detected by multi-frame 2D ultrasound images.

* * * * *